US010068332B2

United States Patent
Zheng et al.

(10) Patent No.: US 10,068,332 B2
(45) Date of Patent: Sep. 4, 2018

(54) PROCESSING A COMPUTED TOMOGRAPHY IMAGE TO REDUCE WINDMILL ARTIFACTS

(71) Applicant: Shenyang Neusoft Medical Systems Co. Ltd., Shenyang (CN)

(72) Inventors: Han Zheng, Shenyang (CN); Shanshan Lou, Shenyang (CN)

(73) Assignee: Shenyang Neusoft Medical Systems Co., Ltd., Shenyang, Liaoning (CN)

( * ) Notice: Subject to any disclaimer, the term of this patent is extended or adjusted under 35 U.S.C. 154(b) by 126 days.

(21) Appl. No.: 15/178,233

(22) Filed: Jun. 9, 2016

(65) Prior Publication Data

US 2016/0364856 A1 Dec. 15, 2016

(30) Foreign Application Priority Data

Jun. 11, 2015 (CN) .......................... 2015 1 0321190
Apr. 12, 2016 (CN) .......................... 2016 1 0228066

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/032* (2013.01); *A61B 6/501* (2013.01); *A61B 6/5211* (2013.01);
(Continued)

(58) Field of Classification Search
None
See application file for complete search history.

(56) References Cited

U.S. PATENT DOCUMENTS 5,529,069 A * 6/1996 Andoh ................. G01R 33/341
324/309
5,845,003 A 12/1998 Hu et al.
(Continued)

FOREIGN PATENT DOCUMENTS

CN 1914644 A 2/2007
CN 103473745 A 12/2013
(Continued)

OTHER PUBLICATIONS

Cheng Chuanle, Application of reconstruction algorithm based on image quality enhancement, China Interv Imaging Ther. 2014, vol. 11, No. 3, p. 188-191.
(Continued)

*Primary Examiner* — Vu Le
*Assistant Examiner* — Samah Beg
(74) *Attorney, Agent, or Firm* — Fish & Richardson P.C.

(57) ABSTRACT

Methods, systems, and apparatus, including computer programs encoded on a computer storage medium, for processing a CT (Computed Tomography) image are provided. An example method includes accessing an original CT image that is reconstructed from a first set of raw data and includes windmill artifacts, generating a high-frequency image by processing the original CT image, generating a low-frequency image by processing a plurality of thick images reconstructed from a second set of raw data and combining the plurality of processed thick images, the second set of raw data including the first set of raw data and each of the plurality of thick images including substantially no windmill artifacts, generating an intermediate image by synthesizing the high-frequency image and the low-frequency image, and obtaining a target CT image based on the generated intermediate image.

20 Claims, 5 Drawing Sheets

(51) Int. Cl.
*A61B 6/03* (2006.01)
*G06K 9/46* (2006.01)
*G06T 5/20* (2006.01)
*G06T 11/00* (2006.01)
*A61B 6/00* (2006.01)

(52) U.S. Cl.
CPC .......... *A61B 6/5258* (2013.01); *G06K 9/4604* (2013.01); *G06T 5/20* (2013.01); *G06T 11/003* (2013.01); *G06T 11/008* (2013.01); *G06T 2207/10081* (2013.01)

(56) References Cited

U.S. PATENT DOCUMENTS

| | | | |
|---|---|---|---|
| 6,600,802 B1 | 7/2003 | Hsieh | |
| 7,623,691 B2 | 11/2009 | Hein et al. | |
| 7,764,763 B2* | 7/2010 | Mori | A61B 6/032 378/11 |
| 7,889,833 B2* | 2/2011 | Hagiwara | G06T 11/008 378/4 |
| 8,938,108 B2* | 1/2015 | Brown | G06T 11/008 250/363.07 |
| 9,406,107 B2* | 8/2016 | Fan | G06T 5/002 |
| 9,675,238 B2* | 6/2017 | Iida | A61B 1/0638 |
| 2001/0012129 A1* | 8/2001 | Inoue | H04N 1/4051 358/2.1 |
| 2002/0186417 A1* | 12/2002 | Inoue | H04N 1/4058 358/3.14 |
| 2003/0076988 A1 | 4/2003 | Liang et al. | |
| 2006/0029285 A1* | 2/2006 | Hein | G06T 5/50 382/260 |
| 2008/0144900 A1* | 6/2008 | Li | G01R 33/4824 382/130 |
| 2009/0110257 A1 | 4/2009 | Hein et al. | |
| 2011/0235942 A1* | 9/2011 | Luo | G06T 5/003 382/275 |
| 2012/0051664 A1* | 3/2012 | Gopalakrishnan | G06T 11/005 382/294 |
| 2012/0189206 A1* | 7/2012 | Iketani | G06T 5/004 382/190 |
| 2013/0041218 A1* | 2/2013 | Iida | A61B 1/0638 600/109 |
| 2016/0183905 A1* | 6/2016 | Lou | A61B 6/583 378/207 |
| 2017/0091917 A1* | 3/2017 | Bronstein | G06T 5/20 |

FOREIGN PATENT DOCUMENTS

| | | |
|---|---|---|
| EP | 2486546 B1 | 5/2014 |
| JP | 2002133399 A | 5/2002 |
| WO | 2013035550 A1 | 3/2013 |

OTHER PUBLICATIONS

State Intellectual Property Office of the People's Republic of China, Office Action and Search Report Issued in Application No. 201610228066.5, dated Feb. 11, 2018, 18 pages (with English-language machine translation, 27 pages).

* cited by examiner

PROCESSING A COMPUTED TOMOGRAPHY IMAGE TO REDUCE WINDMILL ARTIFACTS

CROSS REFERENCE TO RELATED APPLICATIONS

This application claims priority under 35 U.S.C. § 119 to Chinese Applications CN 201510321190.1 filed on Jun. 11, 2015 and CN 201610228066.5, filed on Apr. 12, 2016. The contents of these priority applications are hereby incorporated by reference in their entireties.

TECHNICAL FIELD

The present disclosure is directed to methods, systems, and apparatus for processing a CT (Computed Tomography) image.

BACKGROUND

CT is a technology that adopts X-rays for scanning a certain region of a scanned subject and performs a series of processes on the scanning result to obtain a CT image composed of pixels. The CT image is a type of reconstruction image, and it is also called CT reconstruction image. For example, the scanned subject is a human body. When a helical CT scan is performed on the human body, alternately dark and bright windmill artifacts (also called helical artifacts) may be produced in some organization's position (such as a head or a neck) with rapid changes in a Z-axis direction due to insufficient samplings in the Z-axis direction (also called a cephalopods direction). The occurrence of windmill artifacts may reduce a quality of the CT image, thereby affecting accuracy of a diagnostic result obtained according to the CT image.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

One aspect of the present disclosure features a method of processing a CT image, including accessing an original CT image, wherein the original CT image is reconstructed from a first set of raw data and includes distortion representative of windmill artifacts; generating a high-frequency image by processing the original CT image with a first frequency division process; generating a low-frequency image by processing a plurality of thick images with a second frequency division process and combining the plurality of processed thick images, the plurality of thick images being reconstructed from a second set of raw data that includes the first set of raw data, and each of the plurality of thick images including substantially no distortion representative of windmill artifacts; generating an intermediate image by synthesizing the high-frequency image and the low-frequency image; and obtaining a target CT image based on the generated intermediate image.

In some embodiments, generating a high-frequency image by processing the original CT image with a first frequency division process includes generating frequency domain data for the original CT image by performing a Fourier transform on the original CT image, extracting a high-frequency component from the generated frequency domain data, and generating the high-frequency image by performing an inverse Fourier transform on the extracted high-frequency component. Extracting a high-frequency component from the generated frequency domain data can include: calculating a low-frequency weighting coefficient for each of one or more frequency positions in the generated frequency domain data; calculating a low-frequency value for each of the one or more frequency positions according to a value for the corresponding frequency position in the frequency domain data and the corresponding calculated low-frequency weighting coefficient; generating a high-frequency value for each of the one or more frequency positions by calculating a difference between the value for the frequency position and the corresponding low-frequency value; and assembling the generated high-frequency values for the one or more frequency positions to constitute the high-frequency component in the frequency domain data of the original CT image.

In some implementations, generating a low-frequency image includes determining a thick image reconstruction parameter; reconstructing, according to the determined thick image reconstruction parameter, the plurality of thick images from the second set of raw data; generating a plurality of low-frequency thick images by processing each of the reconstructed thick images with the second frequency division process; and generating the low-frequency image by performing a sharpening combination on the plurality of generated low-frequency thick images. In some cases, the thick image reconstruction parameter includes a reconstruction interval, an image thickness, and an image number. Reconstructing the plurality of thick images includes reconstructing the plurality of thick image from the second set of raw data along a scanning bed direction based on the reconstruction interval, a thickness of each of the reconstructed thick images being the same as the image thickness and a number of the reconstructed thick images being consistent with the image number.

In some cases, generating a plurality of low-frequency thick images by processing each of the reconstructed thick images with the second frequency division process includes: generating frequency domain data for the thick image by performing a Fourier transform on the thick image; extracting a low-frequency component from the generated frequency domain data; and generating a corresponding low-frequency thick image of the thick image by performing an inverse Fourier transform on the extracted low-frequency component.

Extracting a low-frequency component from the generated frequency domain data of the thick image can include: calculating a low-frequency weighting coefficient for each of one or more frequency positions in the generated frequency domain data; calculating a low-frequency value for each of the one or more frequency positions according to a value for the corresponding frequency position in the frequency domain data and the corresponding low-frequency weighting coefficient; and assembling the calculated low-frequency values for the one or more frequency positions to constitute the low-frequency component in the frequency domain data of the thick image.

In some examples, generating the low-frequency image by performing a sharpening combination on the plurality of generated low-frequency thick images includes: determining a corresponding weighting for each of the plurality of low-frequency thick images to be combined; relating, for each of the plurality of low-frequency thick images, a corresponding pixel value to the determined corresponding weighting to generate a corresponding weighted pixel value; and accumulating the weighted pixel values corresponding to an identical pixel of the plurality of low-frequency thick images to generate an accumulated pixel value corresponding to the same pixel of the low-frequency image.

Synthesizing the high-frequency image and the low-frequency image to generate an intermediate image can include adding pixel values corresponding to an identical pixel of the high-frequency image and the low-frequency image to generate a pixel value corresponding to the same pixel of the intermediate image; and generating pixel values for pixels of the intermediate image.

Synthesizing the high-frequency image and the low-frequency image to generate an intermediate image can also include: adding values for an identical frequency position in frequency domain data of the high-frequency image and frequency domain data of the low-frequency image together to generate a value for the same frequency position in frequency domain data of the intermediate image; generating the frequency domain data of the intermediate image based on the generated values for the frequency positions in the frequency domain data; and generating the intermediate image by performing an inverse Fourier transform on the frequency domain data of the intermediate image.

In some cases, obtaining a target CT image based on the intermediate image includes: determining a confidence parameter according to a difference between the intermediate image and the original CT image; and correcting the intermediate image according to the determined confidence parameter and the original CT image to generate a corrected intermediate image as the target CT image.

The second set of raw data including the first set of raw data can be obtained by a detector of a CT scan device in a CT scan for a subject. In some examples, the first set of raw data corresponds to a first scanned region of the subject, the second set of raw data corresponds to a second scanned region of the subject, and the second scanned region covers the first scanned region along a scanning bed direction.

Another aspect of the present disclosure features a CT image processing device including a processor which invokes machine readable instructions corresponding to a CT image processing logic stored on a storage medium and executes the machine readable instructions to perform the method discussed above.

A third aspect of the present disclosure features a non-transitory computer readable storage medium storing instructions executable by a processor and upon such execution cause the processor to perform the method discussed above.

The details of one or more embodiments of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The physics foundation for CT technology is that a difference existed in X-ray absorptions of different objects. A scanned subject (for example, a certain region of a human body) is scanned by X-rays, and the X-rays passing through the region are received by a detector. The received X-rays are photoelectrically converted into an electrical signal, and the electrical signal is converted into a digital signal by an Analog/Digital Converter (ADC). The digital signal may be called raw data, or it may be called a projection data. The raw data is inputted into a computer and is processed by the computer to obtain X-ray attenuation coefficients or X-ray absorption coefficients of all voxels. The X-ray attenuation coefficients are arranged in a digital matrix, wherein each digital number in the digital matrix represents an image value of each pixel, such as a grayscale value. A CT image is constituted by all pixels generated based on the digital matrix. Therefore, the CT image is a type of reconstruction image generated from the raw data obtained by the detector of a CT device, and it is also called a CT reconstruction image in the present disclosure.

Helical (or spiral) CT is a CT technology involving movement in a helical pattern, e.g., for increasing resolution. In some implementations, an x-ray CT scanner images one slice at a time by rotating an X-ray beam and one-dimensional array of detectors while a scanned subject remains static. In some implementations, in helical (or spiral) cone beam CT, the source (e.g., X-ray beam) is conical and has a helical trajectory relative to a scanned subject while a two-dimensional array of detectors measures transmitted radiation on part of a cone of rays emanating from the source. In some helical cone beam x-ray CT devices (or machines), the source and array of detectors can be mounted on a rotating gantry while the subject is moved axially at a uniform rate.

Figure 1A:
FIG. 1A is a diagram of an example of windmill artifacts.

When the CT image is obtained by performing a CT scan, some images actually not existed in the scanned subject may appear in the CT image due to some reasons of the scanning device or the scanned subject, where these images are called artifacts. For example, when a helical (or spiral) CT scan is performed to obtain the CT image, the projection data cannot fully reflect some regions or organizations of the scanned subject with rapid changes in a Z-axis direction due to insufficient samplings in the Z-axis direction, thereby producing radial artifacts in the CT image. For example, FIG. 1A is a diagram of a CT image of a head, where a thickness of the CT image may be 1.25 mm and a pitch of a helical CT scan may be 1.0 mm. The thickness of the CT image means an actual anatomy thickness of the scanned region. When a helical CT scan is adopted to obtain the CT image, the thickness of the CT image may represent a thickness of the scanned region along a scanning bed direction (e.g., the Z-axis direction), and it may be understood as an accumulation of information within a range of the thickness in the Z-axis direction.

As shown in FIG. 1A, since the thickness of the CT image is close to the pitch of the helical CT scan, alternately dark and bright irregular stripes, arranged radially from a high-density tissue (e.g., a bone) acted as a center point to the surrounding areas, are produced in the CT image (as are shown by white arrows). These stripes are called windmill artifacts, which may affect an image quality of low-density soft tissue regions.

Be noted that, the severity of windmill artifacts is related to a thickness of the CT image. For example, the greater the thickness of the CT image, the smaller the impact of windmill artifacts. If the thickness of the CT image is great enough, windmill artifacts may be eliminated. As a result, windmill artifacts may be lowered by increasing a sampling density in the Z-axis or decreasing a pitch of a helical CT scan, where the sampling density in the Z-axis may be increased by changing a focal position of X-rays in the Z-axis with the same projection angle. Further, windmill artifacts may also be eliminated by combining a plurality of CT images.

In order to distinguish the CT image before processing which may include windmill from the processed CT image after processing which may not include any windmill, the CT image before processing (including windmill artifacts) is called "an original CT image", and the processed CT image after processing (eliminating windmill artifacts) is called "a target CT image". When researching the original CT image, we can find that windmill artifacts primarily exist in low-frequency regions of the image. Generally speaking, the low-frequency region of the image includes basic information of the image (e.g., structure information), and the high-frequency region of the image mainly includes image detailed information, such as boundary information, noise information, and etc.

According to an example of the present disclosure, a frequency division may be performed on the original CT image to obtain a high-frequency image, and a frequency division and a combination, e.g., a sharpening combination, are performed on a plurality of thick images to obtain a low-frequency image. The original CT image is reconstructed from a first set of raw data and may include windmill artifacts. The first set of raw data is obtained by a detector of a CT device in a CT scan and may contain windmill artifacts. In some examples, the original CT image may be a portion of an entire CT image reconstructed from the first set of raw data, and the portion of the entire CT image includes windmill artifacts and is used as the original CT image to be processed. In some examples, the original CT image is partially processed to eliminate windmill artifacts.

In some examples, an entire CT image is reconstructed from the first set of raw data and then processed to identify one or more portions that include windmill artifacts. The identified one or more portions can be processed, e.g., using methods as described in the present disclosure, to eliminate windmill artifacts to obtain corresponding target CT image portions. The obtained target CT image portions can be combined (or linked) together with portions of the entire CT image that do not include windmill artifacts to generate a new entire CT image without windmill artifacts.

The plurality of thick images are reconstructed from a second set of raw data obtained by the detector, and each of the plurality of thick images may not include windmill artifacts. The second set of raw data includes the first set of raw data. In some examples, the first set of raw data corresponds to a first scanned region of a subject scanned by a CT scan device along a scanning bed direction, the second set of raw data corresponds to a second scanned region of the subject, and the second scanned region covers the first scanned region along the scanning bed direction. In other words, an anatomy thickness of the first scanned region along the scanning bed direction is smaller than that of the second scanned region. In an example, the first scanned region may locate at the center of the second scanned region.

After that, the high-frequency image and the low-frequency image are synthesized to generate the target CT image. Since the target CT image preserves the high-frequency information of the original CT image, its detailed information won't be affected. Additionally, the windmill artifacts of the low-frequency information of the original CT image are eliminated as far as possible, thereby effectively improving the image quality of the target CT image. In the following description, numerous specific examples are set forth in order to provide a thorough understanding of the present disclosure.

Figure 1B:
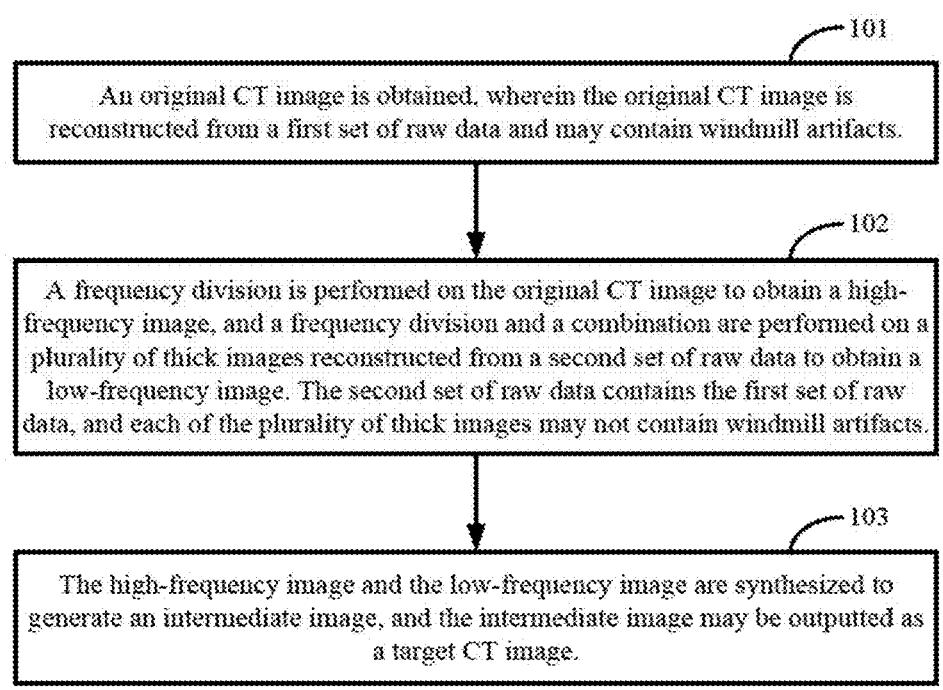
FIG. 1B is a flowchart illustrating procedures of a processing method for CT image according to an example of the present disclosure.

FIG. 1B is a flowchart illustrating the procedures of a processing method for CT image according to an example of the present disclosure. As shown in FIG. 1B, the method may include blocks 101 to 103.

At block 101, an original CT image is obtained, where the original CT image is reconstructed from a first set of raw data and may include windmill artifacts.

At block 102, a frequency division is performed on the original CT image to obtain a high-frequency image, and a frequency division and a combination are performed on a plurality of thick images reconstructed from a second set of raw data to obtain a low-frequency image. The second set of raw data includes the first set of raw data, and each of the plurality of thick images may not include windmill artifacts.

According to an example, a frequency division may be performed on the original CT image directly to obtain the high-frequency image. For example, a Fourier transform may be performed on image information of the original CT image to convert the original CT image from a spatial domain into a frequency domain, i.e., to obtain a frequency domain data of the original CT image, and then a high-frequency component is extracted from a frequency domain data of the original CT image. An inverse Fourier transform is performed on the extracted high-frequency component to generate a high-frequency image of the original CT image.

According to an example, a thick image reconstruction parameter being capable of eliminating windmill artifacts may be determined first according to experiences, where the thick image reconstruction parameter may include a reconstruction interval, an image thickness, and/or an image number, etc. After that, the second set of raw data including the first set of raw data obtained by the detector may be used for reconstructing a plurality of thick images according to the thick image reconstruction parameter, where the plurality of thick images does not include windmill artefacts. A frequency division is performed on the plurality of thick images to obtain a plurality of low-frequency thick images, and a sharpening combination is performed on the plurality of low-frequency thick images to obtain the low-frequency image, where the low-frequency image does not include windmill artifacts. Through the above processes, the obtained low-frequency image does not include windmill artifacts.

At block 103, the high-frequency image and the low-frequency image are synthesized to generate an intermediate image, and the intermediate image may be outputted as a target CT image.

At this block, a value of a predetermined pixel (hereinafter, the value of the pixel may be called "pixel value") of the high-frequency image and a pixel value of the same pixel of the low-frequency image may be added together to obtain a pixel value of the same pixel of the target CT image, thereby obtaining a plurality of pixel values of all pixels of the target CT image so as to constitute the target CT image. According to another example, values at a predetermined frequency position in a frequency domain data of the high-frequency image and a frequency domain data of the low-frequency image may be added together to obtain a value at the same frequency position in a frequency domain data of the target CT image, thereby obtaining the frequency domain data of the target CT image, and an inverse Fourier transform is performed on the frequency domain data of the target CT image to generate the target CT image. Through the abovementioned processes, the low-frequency image not including windmill artifacts and the high-frequency image including detailed information are synthesized to generate the target CT image not including windmill artifacts.

As can be seen from the examples above, the high-frequency image of the original CT image and the low-frequency image (not including windmill artifacts) of the original CT image are obtained by performing a frequency division on the original CT image, and then the high-frequency image and the low-frequency image are synthesized to generate the target CT image not including windmill artifacts, thereby effectively eliminating windmill artifacts of the original CT image and improving the quality of the target CT image, so as to provide a relatively accurate basis for subsequent diagnosis based on the CT image.

Figure 2A:
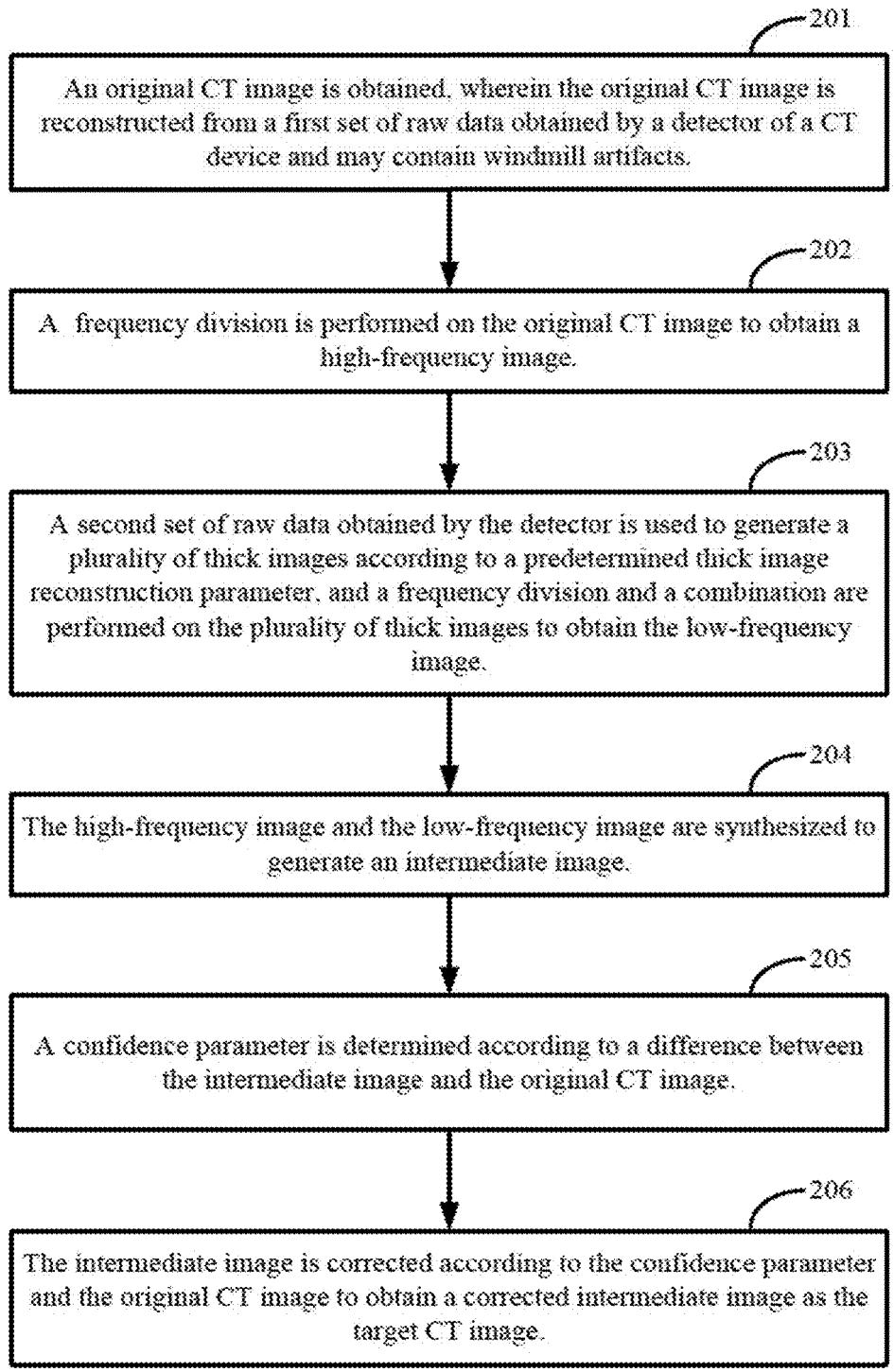
FIG. 2A is a flowchart illustrating procedures of a processing method for CT image according to another example of the present disclosure.

FIG. 2A is a flowchart illustrating the procedures of a processing method for CT image according to another example of the present disclosure. As shown in FIG. 2A, the method may include blocks 201-206.

At block 201, an original CT image is obtained, where the original CT image is reconstructed from a first set of raw data obtained by a detector of a CT device and may include one or more windmill artifacts.

At block 202, a frequency division is performed on the original CT image to obtain a high-frequency image.

The high-frequency region of the original CT image mainly includes image detailed information, such as boundary information, noise information, and etc., where the image detailed information may not be interfered by windmill artifacts. High-frequency information of the original CT image may be obtained by performing a frequency division on the original CT image, and the high-frequency image of the original CT image may be generated based on the high-frequency information.

When performing a frequency division on the original CT image, a Fourier transform may be performed on the image information of the original CT image first to obtain a frequency domain data of the original CT image. After that, a high-frequency component may be extracted from a frequency domain data of the original CT image, and an inverse Fourier transform may be performed on the extracted high-frequency component to generate the high-frequency image of the original CT image. Thereafter, the high-frequency image may be used for synthesizing a target CT image.

When extracting the high-frequency component from the frequency domain data of the original CT image, a low-frequency weighting coefficient at each of frequency positions in the frequency domain data may be calculated first, and a weighted low-frequency value at each of frequency positions may be calculated according to a value at each of frequency positions in the frequency domain data and the corresponding low-frequency weighting coefficient, and then a difference between the value at each of frequency positions and the corresponding weighted low-frequency value may be calculated as a high-frequency value at each of frequency positions.

In some implementations, extracting the high-frequency component from the frequency domain data of the original CT image may be based on a subset of frequency positions in the frequency domain data. For example, a difference between a value at each of the subset of the frequency positions and the corresponding weighted low-frequency value may be calculated as a high-frequency value at each of the subset of the frequency positions.

In an example, a Gaussian function may be adopted to determine the low-frequency weighting coefficients, and the high-frequency component is extracted from the frequency domain data of the image based on the determined low-frequency weighting coefficients. Be noted that, there are many methods for performing a frequency division on the frequency domain data, and adopting other image frequency division methods for separating the high-frequency component and the low-frequency component are not limited in the present disclosure.

Figure 2B:
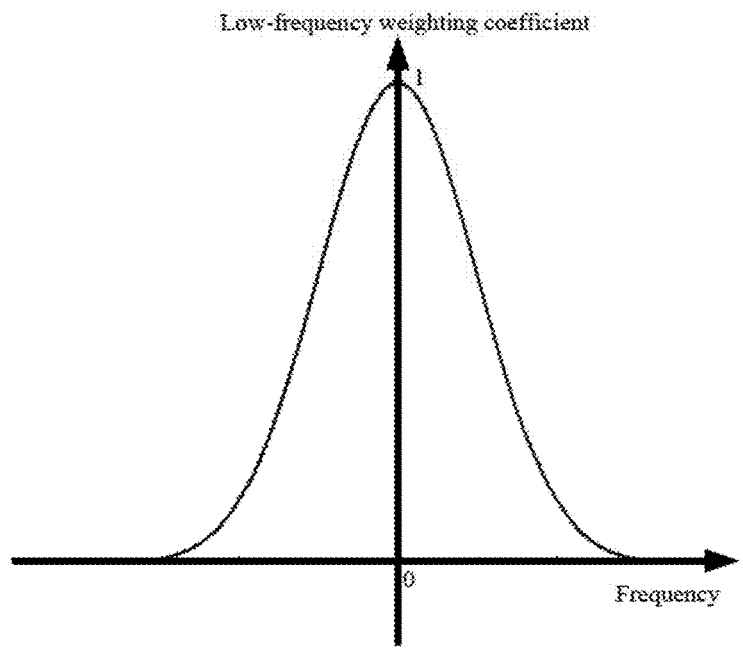
FIG. 2B is an example diagram using a Gaussian function to determine low-frequency weighting coefficients.

FIG. 2B is a diagram using a Gaussian function to determine the low-frequency weighting coefficient. As can be seen from FIG. 2B, the low-frequency weighting coefficient is ranged from 0 to 1, where the lower the absolute value of the frequency, the greater the corresponding low-frequency weighting coefficient; and the greater the absolute value of the frequency, the lower the corresponding low-frequency weighting coefficient.

By combining FIG. 2B, in this example, the following formula may be adopted for calculating the low-frequency weighting coefficient at each of frequency positions in the frequency domain data:

$$FeqWeight = \begin{cases} \dfrac{1}{1 + \left(\dfrac{FeqDisRange}{FeqX}\right)^{2n}} & FeqX > 10^{-6} \\ 1 & FeqX \leq 10^{-6} \end{cases} \quad (1)$$

In the formula above, FeqX represents each of frequency positions in the frequency domain data, FeqWeight represents the low-frequency weighting coefficient at each of frequency positions, FeqDisRange represents a frequency distribution range, and n is a constant. FeqDisRange may be a value of the natural numbers less than 100, for example, the value of FeqDisRange in this example may be 55. The constant n may be a value of the natural numbers less than 5, for example, the value of the constant n in this example may be 2.

After the low-frequency weighting coefficient at each of frequency positions in the frequency domain is calculated, the following formula may be adopted for calculating a weighted low-frequency value at each of frequency positions in the frequency domain data:

$$F_{LowFeq}(FeqX) = FeqWeight(FeqX) \times F(FeqX) \quad (2).$$

In the formula above, FeqWeight (FeqX) represents the low-frequency weighting coefficient of the frequency position FeqX, F (FeqX) represents a value of the frequency position FeqX, and $F_{LowFeq}$(FeqX) represents the weighted low-frequency value of the frequency position FeqX.

The value at each of frequency positions is composed of its corresponding low-frequency value and its corresponding high-frequency value, so the following formula may be adopted for calculating the high-frequency value at each of frequency positions:

$$F_{HighFeq}(FeqX) = F(FeqX) - F_{LowFeq}(FeqX) \quad (3).$$

In the formula above, $F_{HighFeq}$(FeqX) represents the high-frequency value of the frequency position FeqX.

At this block, the formula above may be adopted for calculating the high-frequency value at each of frequency positions in the frequency domain data of the original CT image. The high-frequency values at all frequency positions are assembled, e.g., linked, to constitute the high-frequency component, and then the high-frequency image of the original CT image is generated based on the extracted high-frequency component.

If the high-frequency component extracted from the frequency domain data of the original CT image is regarded as a high-pass filter, the abovementioned method for adopting the Gaussian function to determine the low-frequency weighting coefficient and for calculating the high-frequency value based on the low-frequency weighting coefficient may be regarded as adopting a Gaussian function as the filter function. By contrast, a single-threshold-based division may be regarded as adopting a stepwise function as the filter function. Through performing a frequency division and an extraction based on the low-frequency weighting coefficient, a Concussion effect at discrete points may be appropriately avoided when performing a Fourier transform.

At block 203, a second set of raw data obtained by the detector is used to generate a plurality of thick images according to a predetermined thick image reconstruction parameter, and a frequency division and a combination are performed on the plurality of thick images to obtain the low-frequency image. The second set of raw data includes the first set of raw data from which the original CT image is reconstructed, and each of the plurality of thick images may not include windmill artifacts.

This block 203 may be performed by adopting the following procedures.

First, the thick image reconstruction parameter being capable of eliminating windmill artifacts may be determined according to experiences, where the thick image reconstruction parameter may include a reconstruction interval, an image thickness, and/or an image number, and etc.

As mentioned above, the thickness of the CT image represents an actual anatomy thickness of the scanned region along a scanning bed direction, and it may be understood as an accumulation of information within a range of the thickness along the scanning bed direction. Based on the conception of the accumulation of information, a combination of a certain rule is performed on a plurality of CT images having a first thickness along the scanning bed direction (e.g., the Z-axis direction) so as to obtain an image having a second thickness. If the first thickness is greater than the second thickness, the combination of a certain rule is called a sharpening combination. Hereinafter, based on the conception of the image thickness, an image is called a thin image after a sharpening combination is performed on it. Each of the plurality of images used for combining the thin image is called a thick image. For example, in this present disclosure, the original CT image may be viewed as a thin image, and the thin image (being composed of the thick images) includes pixel information of the original CT image.

Assuming that FilterWidth×2 represents a thickness range of a sharpening combination, a plurality of thick images of an image set not including windmill artifacts may be reconstructed within the thickness range of FilterWidth×2 according to the thick image reconstruction parameter. FilterWidth represents an irradiation width of the scanning X-ray in the Z-axis direction, and all of the plurality of thick images of the image set are arranged according to a certain interval to fill the thickness range of the sharpening combination FilterWidth×2. If the number of the thick images of the image set is enough, a thin image having the consistent reconstruction effect with the original CT image may be obtained by performing a sharpening combination on all of the plurality of thick images of the image set.

In an example of the present disclosure, the reconstruction interval K of the thick image reconstruction parameter may be set as 0.1 mm in advance. Be noted that, the reconstruction interval K may be flexibly adjusted according to actual requirements, and the above mentioned 0.1 mm is merely an example.

The following formula may be adopted for determining the image thickness of the thick image reconstruction parameter, where the image thickness represents a thickness of each of the plurality of thick images of the image set:

$$ThickImage = SliceThick \times Alpha \quad (4).$$

In the formula above, ThickImage represents the image thickness, SliceThick represents a slice thickness of the detector of a CT scan device, and Alpha represents an extension parameter. For the same set of raw data, the greater the thickness of the CT image is, the milder the effect of windmill artifacts is. For example, the value of the extension parameter Alpha may be ranged between 1.2 and 1.8. Assuming that the slice thickness SliceThick of the detector of the CT scan device is 1.25 mm and the extension parameter Alpha is 1.6, the image thickness ThickImage may be 2 mm.

The following formula may be adopted for determining the image number of the thick image reconstruction parameter, where the image number represents a number of thick images of the image set:

$$\text{NumImage} = \frac{\text{FilterWidth} \times 2}{K}. \quad (5)$$

In the formula above, NumImage represents the image number, FilterWidth represents an irradiation range of the X-ray emitted by the CT scan device in the Z-axis direction, FilterWidth×2 represents a thickness range of a sharpening combination, and K represents the reconstruction interval. In an example, assuming that the irradiation range FilterWidth of the X-ray in the Z-axis direction is 10 mm, and the reconstruction interval K is 0.1 mm, and thus the image number NumImage is 200.

When using the determined thick image reconstruction parameter to reconstruct the plurality of thick images of the image set, a second set of raw data including the first set of raw data from which the original CT image is reconstructed may be used for reconstructing the plurality of thick images along the Z-axis direction according to the reconstruction interval. A thickness of each of the plurality of thick images of the image set is the same as the predetermined image thickness, and thus the thick image does not include windmill artifacts. The number of the plurality of thick images of the image set is the same as the predetermined image number.

After the plurality of thick images of the image set is reconstructed, a frequency division process may be used for extracting a low-frequency image set from the image set. For example, a Fourier transform may be performed on the plurality of thick images of the image set to convert the data of the plurality of thick images from a spatial domain into a frequency domain, i.e., to obtain a frequency domain data of the thick images. After that, a low-frequency component in the frequency domain data of the plurality of thick images is extracted, and then a corresponding low-frequency thick image may be obtained by performing an inverse Fourier transform on the extracted low-frequency component. All of the obtained low-frequency thick images may constitute the low-frequency image set.

In an example, when extracting the low-frequency component in the frequency domain data of the plurality of thick images of the image set, a low-frequency weighting coefficient at each of frequency positions in the frequency domain data of the plurality of thick images may be calculated, and a weighted low-frequency value at each of frequency positions may be calculated according to a value at each of frequency positions in the frequency domain data and the corresponding low-frequency weighting coefficient. The specific calculation procedures and examples may be referred to the aforementioned descriptions in block 202, and further description is omitted herein.

Finally, a sharpening combination is performed on the plurality of low-frequency thick images of the low-frequency image set to obtain the low-frequency image. For example, a weighting at any one of the Z-axis position may be determined, and then the weighting at any one of the Z-axis positions may be related to a corresponding pixel value of the low-frequency thick image to obtain a weighted pixel value at any one of the Z-axis positions. For example, the weighting at any one of the Z-axis positions may be multiplied by the corresponding pixel value of the low-frequency thick image to obtain the weighted pixel value at any one of the Z-axis positions. The plurality of weighted pixel values at all of the Z-axis positions is accumulated to obtain an accumulated pixel value acted as a pixel value of the low-frequency image.

Figure 2C:
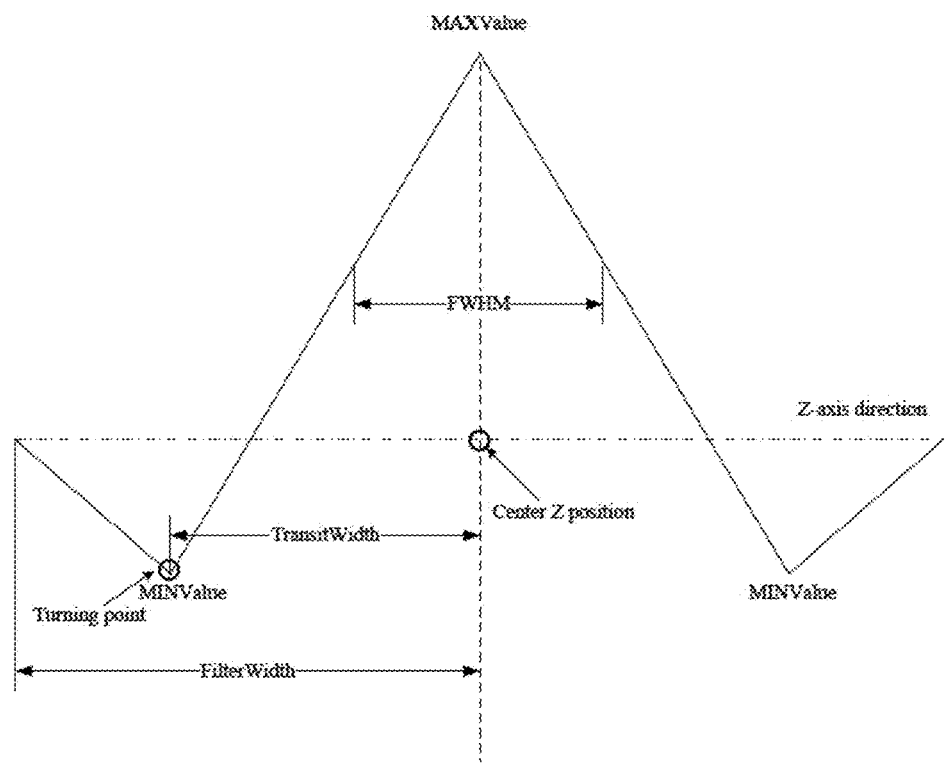
FIG. 2C is a diagram showing an example weighting curve with a sharpening combination.

FIG. 2C is a diagram showing a weighting curve with a sharpening combination. In FIG. 2C, FilterWidth represents a half of a thickness range of the sharpening combination. TransitWidth represents a distance between a turning point and a center Z position, where the center Z position is an image-forming position of the original CT image, and is also called a corresponding Z position of the original CT image hereinafter. MAXValue and MINValue represent a maximum weighting and a minimum weighting, respectively. FWHM represents a thickness of the plurality of thick images used for performing a sharpening combination. The abovementioned parameters meet the following formulas:

$$FWHM = \frac{(MAXValue + MINValue) \times TransitWidth}{MAXValue - MINValue}, \quad (6)$$

$$TransitWidth = \frac{(MAXValue - MINValue) \times FWHM}{MAXValue + MINValue}. \quad (7)$$

After obtaining the plurality of parameters meeting the formulas above, the following formula may be adopted for calculating a weighting at any one of the Z-axis position:

$$\text{Weight}(x) = \quad (8)$$

$$\begin{cases} MAXValue - \dfrac{|x| \times (MAXValue - MINValue)}{TransitWidth} & |x| < TransitWidth \\ 0 & |x| \geq FilterWidth \\ MINValue + \dfrac{|x| - TransitWidth}{FilterWidth - TransitWidth} & TransitWidth \leq |x| < FilterWidth \end{cases}$$

In the formula above, x represents a distance between any one of the Z-axis position and the center Z position, and may also be understood as a distance between an image-forming position of any one of the plurality of thick images and the image-forming position of the original CT image. For example, assuming that the image-forming position of the original CT image is 200 mm, the reconstruction interval K of the thick image reconstruction parameter is 0.1 mm, the image thickness ThickImage is 2 mm, the image number NumImage is 200, and thus the image-forming positions of the plurality of thick images reconstructed according to the thick image reconstruction parameters will have values distributed between [190 mm, 210 mm] with an interval of 0.1 mm, and the distance x will have a value distributed between [−10 mm, 10 mm] with an interval of 0.1 mm. Weight(x) represents a weighting at any one of the Z-axis position, and is also called a corresponding weighting of any one of the plurality of thick images. |x| represent an absolute value of the distance x between any one of the Z-axis position and the center Z position.

After the weighting Weight(x) at any one of the Z-axis position is calculated based on different values of x by adopting the formula above, the following formula may be adopted for calculating a pixel value of a combined image:

$$f_{img} = \sum_{x=-FilterWidth}^{FilterWidth} \text{Weight}(x) \times \text{Val}(x). \quad (9)$$

In the formula above, x represents any one of the Z-axis position, wherein a value of x is ranged between [−FilterWidth, FilterWidth]; $f_{img}$ represents a pixel value of the combined image; Weight(x) represents a weighting at any one of the Z-axis position, that is, a corresponding weighting of x with different values; and Val(x) represents a pixel value of a corresponding image to be combined at any one of the Z-axis position, that is, a corresponding pixel value of x with different values. All of the pixel values obtained according to the abovementioned formula are combined to obtain a low-frequency image having a consistent reconstruction effect with the original CT image.

Be noted that, there is no limitation on the executing order of the abovementioned blocks 202 and 203. For example, the block 203 may be executed first, and then the block 202 is executed; or the blocks 202 and 203 may be executed simultaneously.

At block 204, the high-frequency image and the low-frequency image are synthesized to generate an intermediate image.

After the high-frequency image and the low-frequency image are respectively obtained through the block 202 and the block 203, a Fourier transform may be respectively performed on the high-frequency image and the low-frequency image to obtain the frequency domain data of the high-frequency image and the frequency domain data of the low-frequency image. After that, a value at a predetermined frequency position in the frequency domain data of the high-frequency image and a value at the same frequency position in the frequency domain data of the low-frequency image are added together to obtain a value at the same frequency position in the frequency domain data of the intermediate image, thereby obtaining values at all frequency positions in the frequency domain data of the intermediate image. An inverse Fourier transform may be performed on the frequency domain data of the intermediate image to generate the intermediate image.

In an example, the following formula may be adopted for calculating the pixel value of the intermediate image:

$$f_{Mid}(x) = IFT(F_{HighFeq}(x')) + IFT(F_{LowFeq}(x')) \quad (10).$$

In the formula above, $f_{Mid}(x)$ represents a pixel value at any one of the pixel positions x of the intermediate image; IFT( ) represents an inverse Fourier transform; $F_{HighFeq}(x')$ represents a value at a predetermined frequency position x' in the frequency domain data of the high-frequency image; $F_{LowFeq}(x')$ represents a value at the predetermined frequency position x' in the frequency domain data of the low-frequency image; x' represents the predetermined frequency position (the same frequency position) in the frequency domain data of the high-frequency image and the frequency domain data of the low-frequency image; and the predetermined position x' is corresponding to the pixel positions x of the intermediate image.

In another example, the following formula may be adopted for calculating the pixel value of the intermediate image:

$$f_{Mid}(x) = f_{HighFeq}(x) + f_{LowFeq}(x) \quad (11).$$

In the formula above, $\eta_{Mid}(x)$ represents a pixel value at any one of the pixel positions x of the intermediate image; $f_{HighFeq}(x)$ represents a pixel value at the pixel position x of the high-frequency image; and $f_{LowFeq}(x)$ represents a pixel value at the pixel position x of the low-frequency image.

At block 205, a confidence parameter is determined according to a difference between the intermediate image and the original CT image.

Be compared to the original CT image, windmill artifacts of the synthesized intermediate image are eliminated at block 204. According to an example of the present disclosure, a confidence process may be performed based on a difference between the intermediate image and the original CT image, such that a difference between the target CT image and the original CT image may become as small as possible. For example, a pixel difference value at a predetermined pixel position may be obtained by performing a difference calculation on a pixel value of the predetermined pixel position of the intermediate image and a pixel value of the same pixel position of the original CT image, and then a confidence parameter may be determined based on the pixel difference value.

Figure 2D:
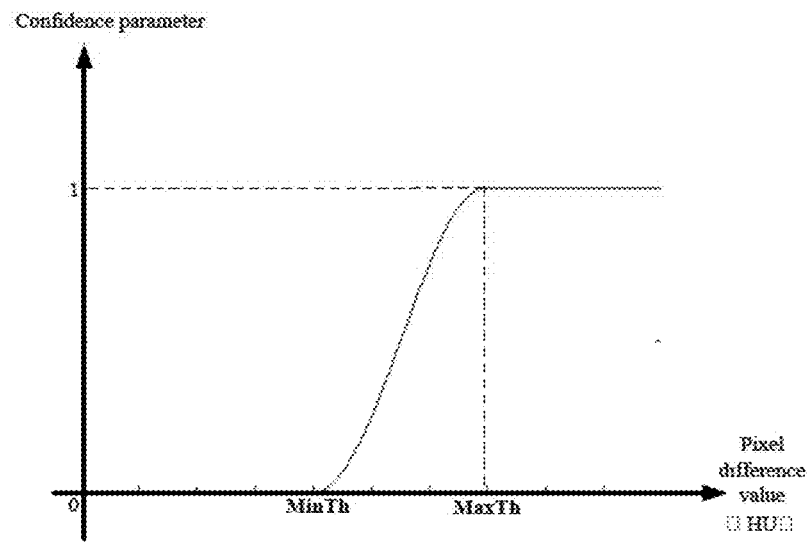
FIG. 2D is an example diagram using pixel difference values to determine a confidence parameter.

FIG. 2D is a diagram using pixel difference values between the intermediate image and the original CT image to determine a confidence parameter. In FIG. 2D, a first threshold MinTh and a second threshold MaxTh are set.

In an alternative example, the value of the first threshold MinTh may be 40, and the value of the second threshold MaxTh may be 70. For the intermediate image and the original CT image, a region having a pixel difference value smaller than the first threshold MinTh may exist windmill artifacts, and thus its corresponding confidence parameter may be set as 0; windmill artifacts may not have a significant impact in a region having a pixel difference value greater than the second threshold MaxTh, and thus its corresponding confidence parameter may be set as 1; and a region having a pixel difference value between the first threshold MinTh and the second threshold MaxTh may be regarded as a transition region, and thus its corresponding confidence parameter may be set based on the pixel difference value in order to ensure a smooth transition of the image.

For example, the confidence parameter may be calculated by adopting the following formula:

$$ImgPorp(x, y) = \begin{cases} 1 & |Diff(x, y)| \geq MaxTh \\ \dfrac{\sin\left(\left(\dfrac{|Diff(x,y)| - MinTh}{MaxTh - MinTh} - \dfrac{1}{2}\right) \times \pi\right)}{2} + \dfrac{1}{2} & MinTh \leq |Diff(x, y)| < MaxTh \\ 0 & |Diff(x, y)| < MinTh \end{cases} \quad (12)$$

In the formula above, ImgPorp(x,y) represents the confidence parameter of the pixel (x,y); and Diff (x,y) represents the pixel difference value at the pixel (x,y) between the intermediate image and the original CT image.

At block 206, the intermediate image is corrected according to the confidence parameter and the original CT image to obtain a corrected intermediate image as the target CT image.

By combining the confidence parameter ImgPorp(x,y) obtained at block 205, the following formula may be adopted for performing an interpolation operation to obtain the pixel value of each of a plurality of pixels of the target CT image:

FinalImg(x,y)=MidImage(x,y)×(1−ImgPorp(x,y))+
    OriImage(x,y)×ImgPorp(x,y)    (13).

In the formula above, OriImage(x,y) represents the pixel value at the pixel (x,y) of the original CT image, MidImage (x,y) represents the pixel value at the pixel (x,y) of the intermediate image, and FinalImg(x,y) represents the pixel value at the pixel (x,y) of the target CT image.

As can be seen from the abovementioned examples, for the original CT image including windmill artifacts, a frequency-division process may be used for obtaining the high-frequency image and the low-frequency image not including windmill artifacts. After the high-frequency image and the low-frequency image are synthesized to generate the intermediate image not including windmill artifacts, the intermediate image is outputted as the target CT image, thereby effectively eliminating windmill artifacts, so as to provide a relatively accurate basis for subsequent diagnosis based on the CT image. Through performing a confidence process based on a difference between the synthesized intermediate image and the original CT image, the corrected intermediate image (e.g., the final target CT image) will be closer to the original CT image, thereby improving the image quality of the target CT image.

Figure 3:
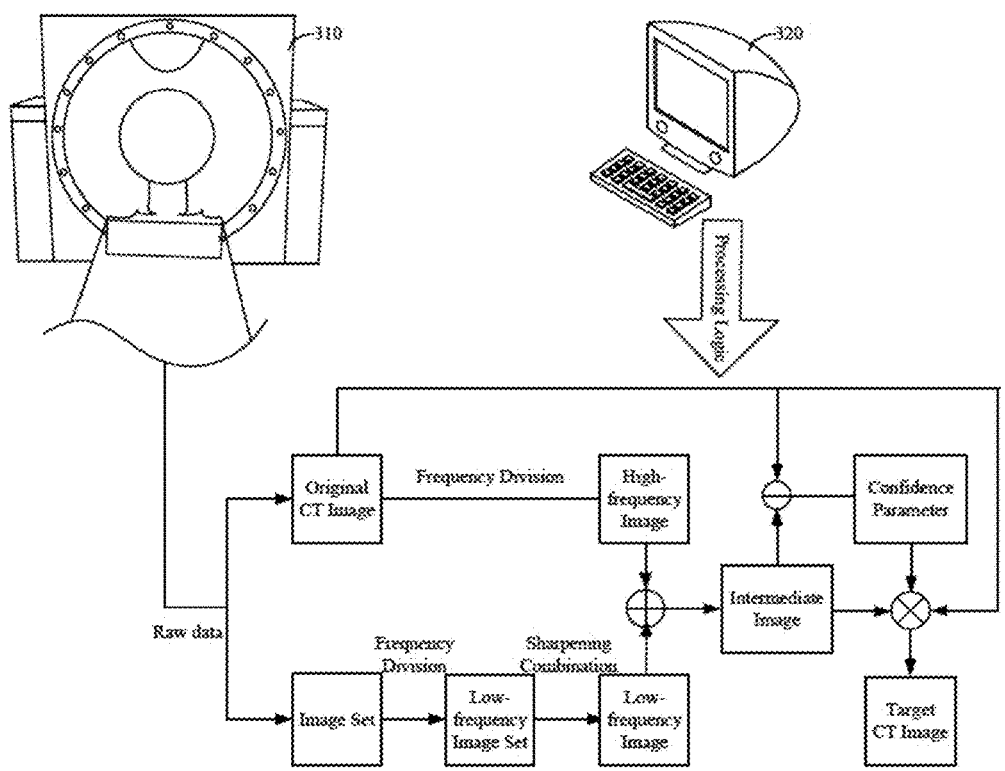
FIG. 3 is a logical architecture diagram of an example CT scan system for performing a CT image process according to an example of the present disclosure.

FIG. 3 is a logical architecture diagram of a CT scan system for performing a CT image process according to an example of the present disclosure.

As shown in FIG. 3, a CT scan system may include a CT device 310 and an image processing device 320. The CT device 310 may use general scanning conditions and reconstruction conditions for scanning a target subject (e.g., a human body) in order to output an original CT image including windmill artifacts. After the image processing device 320 obtains the original CT image, the image processing device 320 processes the original CT image according to the processing logic shown in FIG. 3 to obtain a target CT image not including windmill artifacts. Be noted that, the processing logic is consistent with the procedures of the method shown in FIG. 2A, and further description is omitted herein.

In accordance with the processing method for CT image of the present disclosure, an example of a CT image processing device is provided in the present disclosure.

Figure 4:
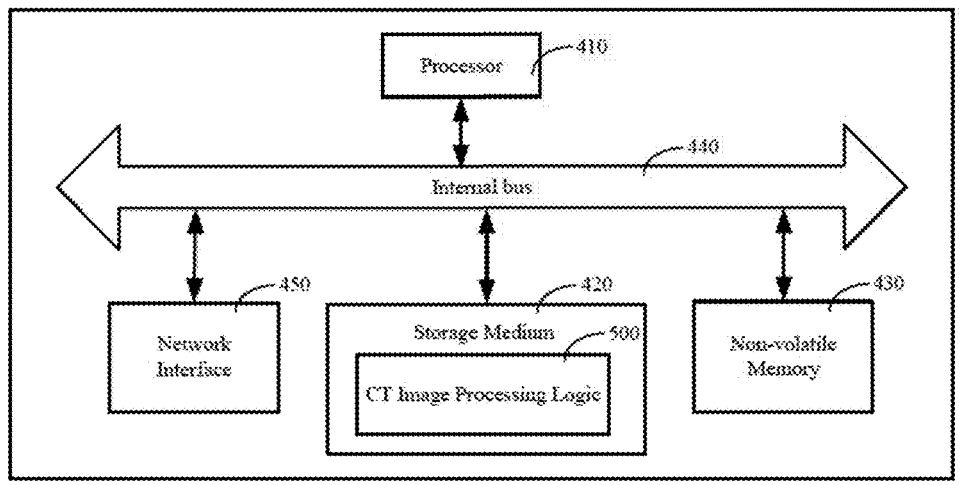
FIG. 4 is a hardware architecture diagram of an example CT image processing device according to an example of the present disclosure.

The example of the CT image processing device of the present disclosure may be applied to a variety of computing devices. FIG. 4 is a hardware architecture diagram of a CT image processing device according to an example of the present disclosure. The CT image processing device may include a processor 410, a storage medium 420, and a non-volatile memory 430. The storage medium 420 and the non-volatile memory 430 are machine readable storage medium, where the processor 410 is connected to the machine readable storage medium 420 and 430 through an internal bus 440. In other possible implementations, the CT image processing device may further include a network interface 450 for communicating with other devices or components. Besides the processor 410, the storage medium 420, the network interface 450, and the non-volatile memory 430, the CT image processing device may further include other hardware based on actual requirements, and is not shown in FIG. 4 anymore.

In different examples, the machine readable storage medium 420 and 430 may be Read Only Memory (ROM), volatile memory, non-volatile memory, flash memory, storage drives (e.g., a hard drive), solid state drive, any type of storage disks (e.g., CD-ROM, DVD, etc.), or similar storage medium, or a combination thereof.

Figure 5:
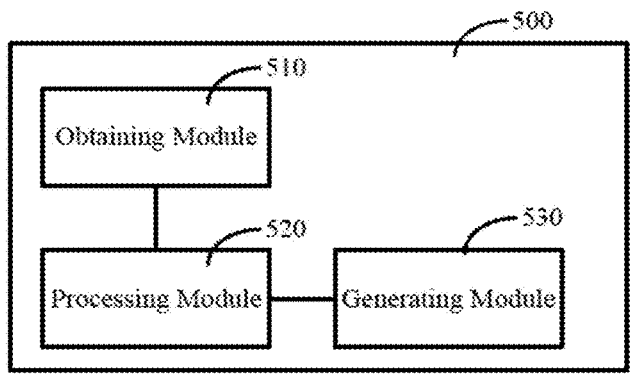
FIG. 5 is a block diagram of a processing logic of an example CT image processing device according to an example of the present disclosure.

In an example, the machine readable storage medium may be embodied as machine readable instructions corresponding to a CT image processing logic 500 stored on a storage medium 420. FIG. 5 is a block diagram of a CT image processing logic 500 of a CT image processing device according to an example of the present disclosure. As shown in FIG. 5, the CT image processing logic 500 may include an obtaining module 510, a processing module 520, and a generating module 530.

The obtaining module 510 is used for obtaining an original CT image, where the original CT image is reconstructed from a first set of raw data and may include windmill artifacts. The processing module 520 is used for performing a frequency division on the original CT image to obtain a high-frequency image, and is used for performing a frequency division and a combination on a plurality of thick images reconstructed from a second set of raw data to obtain a low-frequency image, where the second set of raw data includes the first set of raw data, the original CT image may include windmill artifacts and each of the plurality of thick images may not include windmill artifacts. The generating module 530 is used for synthesizing the high-frequency image and the low-frequency image to generate an intermediate image, and for outputting the intermediate image as a target CT image.

Figure 6:
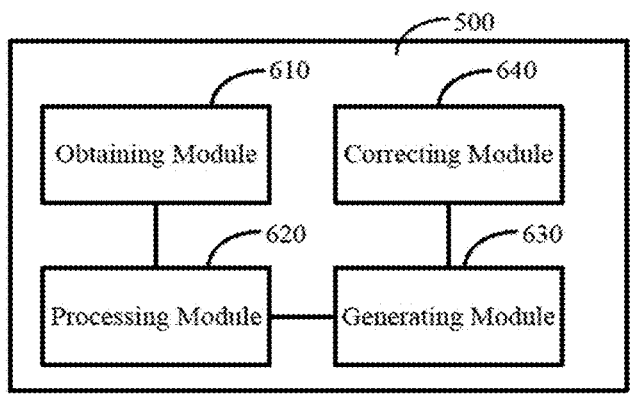
FIG. 6 is a block diagram of a processing logic of a CT image processing device according to another example of the present disclosure.

FIG. 6 is a block diagram of a CT image processing logic of a CT image processing device according to another example of the present disclosure. As shown in FIG. 6, the CT image processing logic 500 may include an obtaining module 610, a processing module 620, a generating module 630, and a correcting module 640.

The obtaining module 610 is used for obtaining an original CT image, wherein the original CT image is reconstructed from a first set of raw data and may include windmill artifacts. The processing module 620 is used for performing a frequency division on the original CT image to obtain a high-frequency image, and is used for performing a frequency division and a combination on a plurality of thick images reconstructed from a second set raw data to obtain a low-frequency image, wherein the second set raw data includes the first set of raw data, the original CT image may include windmill artifacts and each of the plurality of thick images may not include windmill artifacts. The generating module 630 is used for synthesizing the high-frequency image and the low-frequency image to generate an intermediate image. The correcting module 640 is used for determining a confidence parameter according to a difference between the intermediate image and the original CT image, and for correcting the intermediate image according to the determined confidence parameter and the original CT image to obtain a corrected intermediate image. In this case, the generating module 630 may output the corrected intermediate image as the target CT image.

In an example, the processing module 620 may further include (not shown in FIG. 6): an image converting sub-module, a high-frequency component extracting sub-module, and a high-frequency image generating sub-module.

The image converting sub-module is used for performing a Fourier transform on the original CT image to obtain a frequency domain data of the original CT image.

The high-frequency component extracting sub-module is used for extracting a high-frequency component from the frequency domain data of the original CT image.

The high-frequency image generating sub-module is used for performing an inverse Fourier transform on the extracted high-frequency component to generate the high-frequency image of the original CT image.

In an example, the high-frequency component extracting sub-module may be implemented by: calculating a low-frequency weighting coefficient at each of frequency positions in a frequency domain data of the original CT image; calculating a low-frequency value at each of frequency positions according to a value at each of frequency positions in the frequency domain data and the corresponding low-frequency weighting coefficient; and calculating a difference between the value at each of frequency positions and the corresponding low-frequency value as a high-frequency value at each of frequency positions. The high-frequency values at all frequency positions constitute the high-frequency component in the frequency domain data of the original CT image.

In another example, the processing module 620 may further include (not shown in FIG. 6): a parameter determining sub-module, an image reconstruction sub-module, a low-frequency component extracting sub-module, and/or an image combination sub-module.

The parameter determining sub-module is used for determining a thick image reconstruction parameter.

The image reconstruction sub-module is used for using the second set of raw data including the first set of raw data from which the original CT image is reconstructed to reconstruct a plurality of thick images according to the thick image reconstruction parameter, wherein the plurality of thick images may not include windmill artifacts.

The low-frequency component extracting sub-module is used for performing a frequency division on each of the plurality of thick images to obtain a plurality of low-frequency thick images.

The image combination sub-module is used for performing a sharpening combination on the plurality of low-frequency thick images to obtain the low-frequency image.

In an example, the thick image reconstruction parameter may include a reconstruction interval, an image thickness, and an image number. In this case, the image reconstruction sub-module may be implemented by: using the second set of raw data including the first set of raw data from which the original CT image is reconstructed to reconstruct the plurality of thick images along a scanning bed direction based on the reconstruction interval, where a thickness of each of the plurality of thick images is the same as the image thickness, such that each of the plurality of thick images does not include windmill artifacts; and a number of the plurality of thick images is consistent with the image number.

In an example, the low-frequency component extracting sub-module may be implemented by: performing a Fourier transform on the thick image to obtain a frequency domain data of the thick image; extracting a low-frequency component from the frequency domain data of the thick image to be divided; and performing an inverse Fourier transform on the extracted low-frequency component to generate the corresponding low-frequency thick image of the thick image.

In an example, the image combination sub-module may be implemented by: determining a corresponding weighting for each of a plurality of low-frequency thick images to be combined; multiplying all pixel values of each of the low-frequency thick images by the corresponding weighting to obtain a plurality of weighted low-frequency thick images; accumulating pixel values corresponding to an identical pixel of the plurality of weighted low-frequency thick images to obtain a pixel value corresponding to the same pixel of the low-frequency image.

In another example, the generating module 630 may be implemented by: adding pixel values corresponding to an identical pixel of the high-frequency image and the low-frequency image obtain a pixel value corresponding to the same pixel of the intermediate image, thereby obtaining all pixel values of the intermediate image; or adding values at an identical frequency position in a frequency domain data of the high-frequency image and a frequency domain data of the low-frequency image together to obtain a value at the same frequency position in a frequency domain data of the intermediate image, thereby obtaining the frequency domain data of the intermediate image; and performing an inverse Fourier transform on the frequency domain data of the intermediate image to generate the intermediate image.

The implementations of the abovementioned modules and sub-modules may refer to the specific implementing procedures of the corresponding blocks of the method(s) described above, and further description is omitted herein.

The example below is implemented with software, which describes how the CT image processing device runs the processing logic 500. In this example, the processing logic 500 of the present disclosure should be understood as machine readable instructions stored in the machine readable storage medium 420. When the processor 410 of the CT image processing device executes the processing logic 500, the processor 410 executes corresponding machine readable instructions of the processing logic 500 stored in the machine readable storage medium 420 to:

obtain an original CT image, wherein the original CT image is reconstructed from a first set of raw data and includes windmill artifacts;

perform a frequency division on the original CT image to obtain a high-frequency image;

perform a frequency division and a combination on a plurality of thick images reconstructed from a second set of raw data to obtain a low-frequency image, wherein the second set of raw data includes the first set of raw data, and each of the plurality of thick images may not include windmill artifacts; and synthesize the high-frequency image and the low-frequency image to generate an intermediate image, and output the intermediate image as a target CT image.

In an example, when performing a frequency division on the original CT image to obtain a high-frequency image, the machine readable instructions of the processing logic 500 stored in the machine readable storage medium 420 further cause the processor 410 to:

perform a Fourier transform on the original CT image to obtain a frequency domain data of the original CT image;

extract a high-frequency component from the frequency domain data of the original CT image; and perform an inverse Fourier transform on the extracted high-frequency component to generate the high-frequency image.

In an example, when extracting a high-frequency component from a frequency domain data of the original CT image, the machine readable instructions of the processing logic 500 stored in the machine readable storage medium 420 further cause the processor 410 to:

calculate a low-frequency weighting coefficient at each of frequency positions in the frequency domain data;

calculate a low-frequency value at each of frequency positions according to a value at each of frequency positions in the frequency domain data and the corresponding low-frequency weighting coefficient;

calculate a difference between the value at each of frequency positions and the corresponding low-frequency value as a high-frequency value at each of frequency positions; and assemble the high-frequency values at all frequency positions to constitute the high-frequency component in the frequency domain data of the original CT image.

In an example, when performing a frequency division and a combination on a plurality of thick images reconstructed from the second set of raw data to obtain a low-frequency image, the machine readable instructions of the processing logic 500 stored in the machine readable storage medium 420 further cause the processor 410 to:

determine a thick image reconstruction parameter;

use the second set of raw data including the first set of raw data to reconstruct the plurality of thick images according to the thick image reconstruction parameter; and perform a frequency division on each of the plurality of thick images to obtain a plurality of low-frequency thick images, and perform a sharpening combination on the plurality of low-frequency thick images to obtain the low-frequency image.

In an example, the thick image reconstruction parameter may include a reconstruction interval, an image thickness, and an image number. Under this condition, when using the second set of raw data to reconstruct the plurality of thick images according to the thick image reconstruction parameter, the machine readable instructions of the processing logic 500 stored in the machine readable storage medium 420 further cause the processor 410 to:

use the second set of raw data including the first set of raw data to reconstruct the plurality of thick images along a scanning bed direction based on the reconstruction interval. A thickness of each of the plurality of thick images is the same as the image thickness, and thus each of the plurality of thick image does not include windmill artifacts. A number of the plurality of thick images is consistent with the image number.

In an example, when performing a frequency division on each of the plurality of thick images to obtain a plurality of low-frequency thick images, the machine readable instructions of the processing logic 500 stored in the machine readable storage medium 420 further cause the processor 410 to:

perform a Fourier transform on the thick image to be divided to obtain a frequency domain data of the thick image;

extract a low-frequency component from the frequency domain data of the thick image; and perform an inverse Fourier transform on the extracted low-frequency component to generate the corresponding low-frequency thick image of the thick image.

In an example, when extracting a low-frequency component from the frequency domain data of the thick image, the machine readable instructions of the processing logic 500 stored in the machine readable storage medium 420 further cause the processor 410 to:

calculate a low-frequency weighting coefficient at each of frequency positions in the frequency domain data;

calculate a low-frequency value at each of frequency positions according to a value at each of frequency positions in the frequency domain data and the corresponding low-frequency weighting coefficient; and assemble the low-frequency values at all frequency positions to constitute the low-frequency component in the frequency domain data of the thick image.

In an example, when performing a sharpening combination on the plurality of low-frequency thick images to obtain the low-frequency image, the machine readable instructions of the processing logic 500 stored in the machine readable storage medium 420 further cause the processor 410 to:

determine a corresponding weighting for each of a plurality of low-frequency thick images to be combined;

multiply all pixel values of each of the low-frequency thick images by the corresponding weighting to obtain a plurality of weighted low-frequency thick images;

accumulate pixel values corresponding to an identical pixel of the plurality of weighted low-frequency thick images to obtain a pixel value corresponding to the same pixel of the low-frequency image.

In an example, when synthesizing the high-frequency image and the low-frequency image to generate an intermediate image, the machine readable instructions of the processing logic 500 stored in the machine readable storage medium 420 further cause the processor 410 to:

add pixel values corresponding to an identical pixel of the high-frequency image and the low-frequency image obtain a pixel value corresponding to the same pixel of the intermediate image, thereby obtaining all pixel values of the intermediate image; or add values at an identical frequency position in a frequency domain data of the high-frequency image and a frequency domain data of the low-frequency image together to obtain a value at the same frequency position in a frequency domain data of the intermediate image, thereby obtaining the frequency domain data of the intermediate image; and perform an inverse Fourier transform on the frequency domain data of the intermediate image to generate the intermediate image.

In an example, when outputting the intermediate image as a target CT image, the machine readable instructions of the processing logic 500 stored in the machine readable storage medium 420 further cause the processor 410 to:

determine a confidence parameter according to a difference between the intermediate image and the original CT image;

correct the intermediate image according to the determined confidence parameter and the original CT image to obtain a corrected intermediate image; and output the corrected intermediate image as the target CT image.

As can be seen from the examples above, the high-frequency image of the original CT image and the low-frequency image (not including windmill artifacts) of the original CT image are obtained by performing a frequency division on the original CT image, and then the high-frequency image and the low-frequency image are synthesized to generate the target CT image not including windmill artifacts, thereby effectively improving the quality of the target CT image, so as to provide a relatively accurate basis for subsequent diagnosis based on the CT image.

The above are only preferred examples of the present disclosure is not intended to limit the disclosure within the spirit and principles of the present disclosure, any changes made, equivalent replacement, or improvement in the protection of the present disclosure should include within the range.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of processing a Computed Tomography (CT) image, comprising:
    accessing an original CT image, wherein the original CT image is reconstructed from a first set of raw data and includes distortion representative of windmill artifacts;
    generating a high-frequency image by processing the original CT image with a first frequency division process;
    generating a low-frequency image by processing a plurality of thick images with a second frequency division process and combining the plurality of processed thick images, wherein the plurality of thick images is reconstructed from a second set of raw data that includes the first set of raw data, and each of the plurality of thick images includes substantially no distortion representative of windmill artifacts;
    generating an intermediate image by synthesizing the high-frequency image and the low-frequency image; and
    obtaining a target CT image based on the generated intermediate image.

2. The method of claim 1, wherein generating a high-frequency image by processing the original CT image with a first frequency division process comprises:
    generating frequency domain data for the original CT image by performing a Fourier transform on the original CT image;
    extracting a high-frequency component from the generated frequency domain data; and
    generating the high-frequency image by performing an inverse Fourier transform on the extracted high-frequency component.

3. The method of claim 2, wherein extracting a high-frequency component from the generated frequency domain data comprises:
    calculating a low-frequency weighting coefficient for each of one or more frequency positions in the generated frequency domain data;
    calculating a low-frequency value for each of the one or more frequency positions according to a value for the corresponding frequency position in the frequency domain data and the corresponding calculated low-frequency weighting coefficient;
    generating a high-frequency value for each of the one or more frequency positions by calculating a difference between the value for the frequency position and the corresponding low-frequency value; and
    assembling the generated high-frequency values for the one or more frequency positions to constitute the high-frequency component in the frequency domain data of the original CT image.

4. The method of claim 1, wherein generating a low-frequency image comprises:
    determining a thick image reconstruction parameter;
    reconstructing, according to the determined thick image reconstruction parameter, the plurality of thick images from the second set of raw data;
    generating a plurality of low-frequency thick images by processing each of the reconstructed thick images with the second frequency division process; and
    generating the low-frequency image by performing a sharpening combination on the plurality of generated low-frequency thick images.

5. The method of claim 4, wherein the thick image reconstruction parameter comprises a reconstruction interval, an image thickness, and an image number,
    wherein reconstructing the plurality of thick images comprises reconstructing the plurality of thick images from the second set of raw data along a scanning bed direction based on the reconstruction interval, a thickness of each of the reconstructed thick images being the same as the image thickness and a number of the reconstructed thick images being consistent with the image number.

6. The method of claim 4, wherein generating a plurality of low-frequency thick images by processing each of the reconstructed thick images with the second frequency division process comprises:
    generating frequency domain data for the thick image by performing a Fourier transform on the thick image;
    extracting a low-frequency component from the generated frequency domain data; and
    generating a corresponding low-frequency thick image of the thick image by performing an inverse Fourier transform on the extracted low-frequency component.

7. The method of claim 6, wherein extracting a low-frequency component from the generated frequency domain data comprises:
    calculating a low-frequency weighting coefficient for each of one or more frequency positions in the generated frequency domain data;
    calculating a low-frequency value for each of the one or more frequency positions according to a value for the corresponding frequency position in the frequency domain data and the corresponding low-frequency weighting coefficient; and assembling the calculated low-frequency values for the one or more frequency positions to constitute the low-frequency component in the frequency domain data of the thick image.

8. The method of claim 4, wherein generating the low-frequency image by performing a sharpening combination on the plurality of generated low-frequency thick images comprises:
   determining a corresponding weighting for each of the plurality of low-frequency thick images to be combined;
   relating, for each of the plurality of low-frequency thick images, a corresponding pixel value to the determined corresponding weighting to generate a corresponding weighted pixel value; and
   accumulating the weighted pixel values corresponding to an identical pixel of the plurality of low-frequency thick images to generate an accumulated pixel value corresponding to the same pixel of the low-frequency image.

9. The method of claim 1, wherein synthesizing the high-frequency image and the low-frequency image comprises one of:
   adding pixel values corresponding to an identical pixel of the high-frequency image and the low-frequency image to generate a pixel value corresponding to the same pixel of the intermediate image, and generating pixel values for pixels of the intermediate image, and
   adding values for an identical frequency position in frequency domain data of the high-frequency image and frequency domain data of the low-frequency image together to generate a value for the same frequency position in frequency domain data of the intermediate image, generating the frequency domain data of the intermediate image based on the generated values for the frequency positions in the frequency domain data, and generating the intermediate image by performing an inverse Fourier transform on the generated frequency domain data.

10. The method of claim 1, wherein obtaining a target CT image based on the intermediate image comprises:
    determining a confidence parameter according to a difference between the intermediate image and the original CT image; and
    correcting the intermediate image according to the determined confidence parameter and the original CT image to generate a corrected intermediate image as the target CT image.

11. The method of claim 1, wherein the second set of raw data including the first set of raw data is obtained by a detector of a CT scan device in a CT scan for a subject,
    wherein the first set of raw data corresponds to a first scanned region of the subject, the second set of raw data corresponds to a second scanned region of the subject, and the second scanned region covers the first scanned region along a scanning bed direction, and
    wherein a first anatomy thickness of the first scanned region along the scanning bed direction is smaller than a second anatomy thickness of the second scanned region along the scanning bed direction.

12. A CT image processing device comprising:
    a processor which invokes machine readable instructions corresponding to a CT image processing logic stored on a storage medium and executes the machine readable instructions to:
    access an original CT image, wherein the original CT image is reconstructed from a first set of raw data and includes distortion representative of windmill artifacts;
    generate a high-frequency image by processing the original CT image with a first frequency division process;
    generate a low-frequency image by processing a plurality of thick images with a second frequency division process and combining the plurality of processed thick images, wherein the plurality of thick images is reconstructed from a second set of raw data that includes the first set of raw data, and each of the plurality of thick images includes substantially no distortion representative of windmill artifacts;
    generate an intermediate image by synthesizing the high-frequency image and the low-frequency image; and
    obtain a target CT image based on the generated intermediate image.

13. The device of claim 12, wherein, when generating a high-frequency image by processing the original CT image with a first frequency division process, the machine readable instructions further cause the processor to:
    generate frequency domain data for the original CT image by performing a Fourier transform on the original CT image;
    extract a high-frequency component from the generated frequency domain data; and
    generate the high-frequency image by performing an inverse Fourier transform on the extracted high-frequency component.

14. The device of claim 13, wherein, when extracting a high-frequency component from the generated frequency domain data, the machine readable instructions further cause the processor to:
    calculate a low-frequency weighting coefficient for each of one or more frequency positions in the generated frequency domain data;
    calculate a low-frequency value for each of the one or more frequency positions according to a value for the corresponding frequency position in the frequency domain data and the corresponding calculated low-frequency weighting coefficient;
    generate a high-frequency value for each of the one or more frequency positions by calculating a difference between the value for the frequency position and the corresponding low-frequency value; and
    assemble the generated high-frequency values for the one or more frequency positions to constitute the high-frequency component in the frequency domain data of the original CT image.

15. The device of claim 12, wherein, when generating a low-frequency image, the machine readable instructions further cause the processor to:
    determine a thick image reconstruction parameter;
    reconstruct, according to the determined thick image reconstruction parameter, the plurality of thick images from the second set of raw data;
    generate a plurality of low-frequency thick images by processing each of the reconstructed thick images with the second frequency division process; and
    generate the low-frequency image by performing a sharpening combination on the plurality of generated low-frequency thick images.

16. The device of claim 15, wherein the thick image reconstruction parameter comprises a reconstruction interval, an image thickness, and an image number, wherein, when reconstructing the plurality of thick images, the machine readable instructions cause the processor to:

reconstruct the plurality of thick images from the second set of raw data along a scanning bed direction based on the reconstruction interval, a thickness of each of the reconstructed thick images being the same as the image thickness and a number of the reconstructed thick images being consistent with the image number.

17. The device of claim 15, wherein, when generating a plurality of low-frequency thick images by processing each of the reconstructed thick images with the second frequency division process, the machine readable instructions further cause the processor to:

generate frequency domain data for the thick image by performing a Fourier transform on the thick image;

extract a low-frequency component from the generated frequency domain data of the thick image; and generate a corresponding low-frequency thick image of the thick image by performing an inverse Fourier transform on the extracted low-frequency component.

18. The device of claim 17, wherein, when extracting a low-frequency component from the generated frequency domain data, the machine readable instructions further cause the processor to:

calculate a low-frequency weighting coefficient for each of one or more frequency positions in the generated frequency domain data;

calculate a low-frequency value for each of the one or more frequency positions according to a value for the corresponding frequency position in the frequency domain data and the corresponding low-frequency weighting coefficient; and assemble the calculated low-frequency values for the one or more frequency positions to constitute the low-frequency component in the frequency domain data of the thick image.

19. The device of claim 15, wherein, when generating the low-frequency image by performing a sharpening combination on the plurality of generated low-frequency thick images, the machine readable instructions further cause the processor to:

determine a corresponding weighting for each of the plurality of low-frequency thick images to be combined;

relate, for each of the plurality of low-frequency thick images, a corresponding pixel value to the determined corresponding weighting to generate a corresponding weighted pixel value; and accumulate the weighted pixel values corresponding to an identical pixel of the plurality of low-frequency thick images to generate an accumulated pixel value corresponding to the same pixel of the low-frequency image.

20. A non-transitory computer readable storage medium storing instructions executable by a processor and upon such execution cause the processor to:

access an original CT image, wherein the original CT image is reconstructed from a first set of raw data and includes distortion representative of windmill artifacts;

generate a high-frequency image by processing the original CT image with a first frequency division process;

generate a low-frequency image by processing a plurality of thick images with a second frequency division process and combining the plurality of processed thick images, wherein the plurality of thick images is reconstructed from a second set of raw data that includes the first set of raw data, and each of the plurality of thick images includes substantially no distortion representative of windmill artifacts;

generate an intermediate image by synthesizing the high-frequency image and the low-frequency image; and obtain a target CT image based on the generated intermediate image.

* * * * *